United States Patent [19]

Gleason et al.

[11] Patent Number: 4,730,005
[45] Date of Patent: Mar. 8, 1988

[54] LEUKOTRIENE ANTAGONIST

[75] Inventors: John G. Gleason, Delran, N.J.; Carl D. Perchonock, Philadelphia, Pa.

[73] Assignee: SmithKline Beckman Corporation, Philadelphia, Pa.

[21] Appl. No.: 864,562

[22] Filed: May 16, 1986

Related U.S. Application Data

[63] Continuation of Ser. No. 716,320, Mar. 27, 1985, abandoned, which is a continuation-in-part of Ser. No. 689,114, Jan. 7, 1985, abandoned, which is a continuation-in-part of Ser. No. 630,500, Jul. 13, 1984, abandoned, which is a continuation-in-part of Ser. No. 572,021, Jan. 19, 1984, abandoned.

[51] Int. Cl.[4] .................. A61K 31/38; C07D 333/36; C07D 333/32; C07D 333/24
[52] U.S. Cl. ................... 514/438; 514/445; 514/447; 514/570; 549/63; 549/66; 549/68; 549/79; 562/426; 562/429; 562/430
[58] Field of Search .................. 549/63, 66, 71, 79, 549/68; 562/426, , 429, 430; 514/438, 445, 447, 570

[56] References Cited

U.S. PATENT DOCUMENTS

| | | | |
|---|---|---|---|
| 3,078,290 | 2/1963 | Hechenbleikner | 260/429.7 |
| 4,111,873 | 9/1978 | Cordes | 260/23 X A |
| 4,134,879 | 1/1979 | Schmidt | 260/45.85 P |
| 4,269,731 | 5/1981 | Mack | 252/400 R |
| 4,348,383 | 9/1982 | Bouillon | 424/70 |

FOREIGN PATENT DOCUMENTS

| | | |
|---|---|---|
| 0024919 | 3/1981 | European Pat. Off. |
| 94613 | 3/1978 | Japan |

OTHER PUBLICATIONS

Kogo et al. Chem. Abst. 89:130417 (1978).
Chemical Abstracts, vol. 85, 1976, 32188 No. 32190h, Pesek.
Chemical Abstracts, vol. 71, 1969, 74821 No. 74808g, Canonne

*Primary Examiner*—Alan Siegel
*Attorney, Agent, or Firm*—Nancy S. Mayer; Janice E. Williams; Alan D. Lourie

[57] ABSTRACT

The compounds represented by the following structural formula (I)

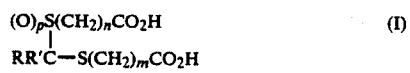

wherein m is 1 or 2; n is 1, 2 or 3; R' is hydrogen or methyl; R is a radical selected from the group consisting of:

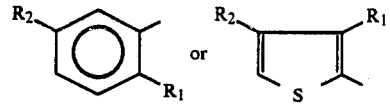

wherein $R_1$ is $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecynyl, 1-trans-dodecenyl, 5-(4-acetyl-3-hydroxy-2-propyl-phenoxypentoxy, 2(Z), 5(Z)-undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl-CH=CH—(CH$_2$)$_{2-8}$, phenyl-$C_3$ to $C_9$ alkoxy, trifluoromethyl-$C_7$ to $C_{12}$ alkyl, cyclohexyl- $C_4$ to $C_{10}$ alkyl or

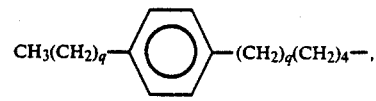

wherein each q is 0, 1, 2 or 3 but the sum of both q's does not exceed 3, and $R_2$ is hydrogen, bromo, chloro, methyl, trifluoromethyl, hydroxy, methoxy or nitro; or $R_1$ is hydrogen and $R_2$ is $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecynyl, 1-trans-dodecenyl, 5-(4-acetyl-3-hydroxy-2-propylphenoxy(pentoxy, 2(Z), 5(Z)-undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl-CH=CH—(CH$_2$)$_{2-8}$, phenyl-$C_3$ to $C_9$ alkoxy, trifluoromethyl-$C_7$ to $C_{12}$ alkyl, cyclohexyl-$C_4$ to $C_{10}$ alkyl or wherein each q is 0, 1, 2 or 3 but the sum of both q's does not exceed 3, and p is 0 or 1, with the proviso that R is not a thiophene radical and any of $R_1$ and $R_2$ above are not thioalkyl or phenylthioalkyl when p is 1; and pharmaceutically acceptable salts thereof have been found to be leukotriene antagonists and useful in the treatment of diseases in which leukotrienes are a factor, such as asthma.

22 Claims, No Drawings

LEUKOTRIENE ANTAGONIST

This is a continuation of application Ser. No. 716,320 filed Mar. 27, 1985 now abandoned, which is a continuation-in-part of application Ser. No. 689,114 filed Jan. 7, 1985, now abandoned, which is a continuation-in-part of application Ser. No. 630,500 filed July 13, 1984, now abandoned, which is a continuation-in-part of application Ser. No. 572,021 filed Jan. 19, 1984, now abandoned.

BACKGROUND OF THE INVENTION

"Slow Reacting Substance of Anaphylaxis" (SRS-A) has been shown to be a highly potent bronchoconstricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of the cardiovascular effects of histamine.

The discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$ ($LTC_4$), leukotriene-$D_4$ ($LTD_4$) and leukotriene-$E_4$ ($LTE_4$), the structural formulae of which are represented below.

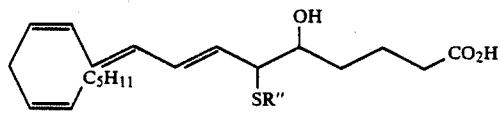

$LTC_4\ R'' = $ Cys—Gly (γ-Glu)
$LTD_4\ R'' = $ Cys—Gly
$LTE_4\ R'' = $ Cys

By antagonizing the effects of $LTC_4$, $LTD_4$ and $LTE_4$ or other pharmacologically active mediators at the end organ, e.g. airway smooth muscle, the compounds and pharmaceutical compositions of the instant invention are valuable in the treatment of diseases in which leukotrienes are a factor, such as asthma.

DETAILED DESCRIPTION OF THE INVENTION

The compounds of this invention are represented by the following general structural formula (I)

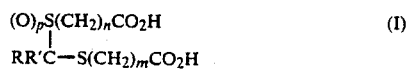

wherein m is 1 or 2; n is 1, 2 or 3; R' is hydrogen or methyl; R is a radical selected from the group consisting of:

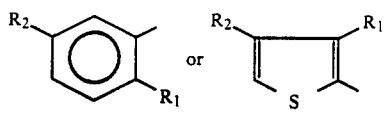

wherein $R_1$ is $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecenyl, 1-trans-dodecenyl, 5-(4-acetyl-3-hydroxy-2-propylphenoxy)pentoxy, 2(Z),5(Z),5(Z)undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl—CH=CH—$(CH_2)_{2-8}$, phenyl-$C_3$ to $C_9$ alkoxy, trifluoromethyl-$C_7$ to $C_{12}$ alkyl, cyclohexyl-$C_4$ to $C_{10}$ alkyl or

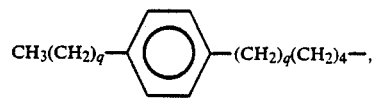

wherein each q is 0, 1, 2 or 3 but the sum of both q's does not exceed 3, and $R_2$ is hydrogen, bromo, chloro, methyl, trifluoromethyl, hydroxy, methoxy or nitro; or $R_1$ is hydrogen and $R_2$ is $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecynyl, 1-trans-dodecenyl, 5-(4-acetyl-3-hydroxy-2-propylphenoxy)-pentoxy, 2(Z),5(Z)-undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl —CH=CH—$(CH_2)_{2-8}$, phenyl-$C_3$ to $C_9$ alkoxy, tri-fluoromethyl-$C_7$ to $C_{12}$ alkyl, cyclohexyl-$C_4$ to $C_{10}$ alkyl, or

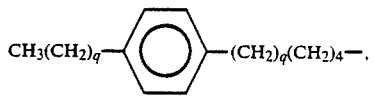

wherein each q is 0, 1, 2 or 3 but the sum of both q's does not exceed 3, and p is 0 or 1, with the proviso that R is not a thiophene radical and any of $R_1$ and $R_2$ above are not thioalkyl or phenylthioalkyl when p is 1, and pharmaceutically acceptable salts thereof.

A particular class of compounds of this invention are the substituted phenyldioic acid analogs of formula (I) wherein R' is hydrogen and R is the phenyl radical and are represented by the structural formula (II)

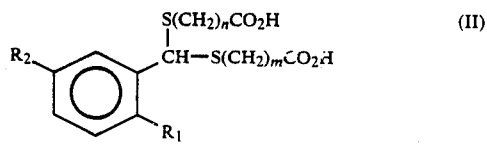

wherein m, n, $R_1$ and $R_2$ are described above.

Particular members of this class of compounds are those represented by the structural formula (II) wherein $R_1$ is selected from the group consisting of $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecynyl, 1-trans-dodecenyl, 5-(4-acetyl-3-hydroxy-2-propyl-phenoxy)-pentoxy, 2(Z),5(Z)-undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl—CH=CH—$(CH_2)_{2-8}$, phenyl—$C_3$ to $C_9$ alkoxy, trifluoromethyl-$C_7$ to $C_{12}$ alkyl, cyclohexyl-$C_4$ to $C_{10}$ alkyl, and

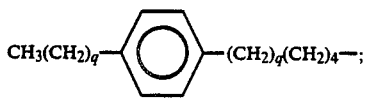

$R_2$ is hydrogen, bromo, chloro, methyl, trifluoromethyl, hydroxy, methoxy, or nitro and m, n and q are described above.

A subgeneric class of these compounds are the 4,6-dithianonanedioic acid derivatives represented by the following general structural formula (III)

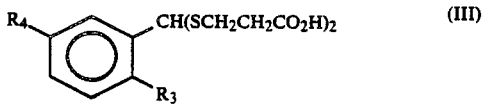

wherein $R_3$ is selected from the group consisting of $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecynyl, 1-trans-dodecenyl, 5-(4-acetyl-3-hydroxy-2-propyl-phenoxy)-pentoxy, 2(Z),5(Z)- undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl—CH=CH—$(CH_2)_{2-8}$, phenyl-$C_3$ to $C_9$ alkoxy, trifluoromethyl-$C_7$ to $C_{12}$ alkyl, cyclohexyl-$C_4$ to $C_{10}$ alkyl, and

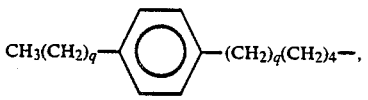

$R_4$ is hydrogen, bromo, chloro, methyl, trifluoromethyl, hydroxy, methoxy or nitro and q is described above.

The compounds of the formula (III) wherein $R_4$ is hydrogen are exemplified by the following classes of compounds:

(A) where $R_3$ is an alkyl radical containing from 8 to 13 carbon atoms:
 (1) 4,6-dithia-5-(2-dodecylphenyl)nonanedioic acid;
 (2) 4,6-dithia-5-(2-decylphenyl)nonanedioic acid; and
 (3) 4,6-dithia-5-(2-octylphenyl)nonanedioic acid;

(B) where $R_3$ is an alkoxy radical containing from 7 to 12 carbon atoms:
 (1) 4,6-dithia-5-(2-undecyloxyphenyl)nonanedioic acid; and
 (2) 4,6-dithia-5-(2-nonyloxyphenyl)nonanedioic acid;

(C) where $R_3$ is a thioalkyl radical containing from 7 to 12 carbon atoms or a 1-alkynyl radical containing from 10 to 12 carbon atoms:

(1) 4,6-dithia-5-(2-undecylthiophenyl)nonanedioic acid; and
 (2) 4,6-dithia-5-[2-(1-dodecyn-1-yl)phenyl]nonanedioic acid;

(D) where $R_3$ is an 2(Z),5(Z)-undecadienyloxy radical:
 4,6-dithia-5-[2-(2(Z),5(Z)-undecadienyloxy)phenyl]-nonanedioic acid;

(E) where $R_3$ is a phenyl-$C_4$ to $C_{10}$ alkyl radical (optionally substituted), phenylthio-$C_3$ to $C_9$ alkyl radical (optionally substituted), phenyl-$C_3$ to $C_9$ alkoxy radical or cyclohexyl-$C_4$ to $C_{10}$ alkyl radical:
 (1) 4,6-dithia-5-[2-(8-phenyloctyl)phenyl]nonanedioic acid;
 (2) 4,6-dithia-5-[2-(6-phenylhexyloxy)phenyl]-nonanedioic acid;
 (3) 4,6-dithia-5-[2-(8-cyclohexyloctyl)phenyl]-nonanedioic acid;
 (4) 4,6-dithia-5-[2-(8-(4-trifluoromethylphenyl)octyl)-phenyl]nonanedioic acid; and
 (5) 4,6-dithia-5-[2-(7-phenylthioheptyl)phenyl]-nonanedioic acid;

(F) where $R_3$ is a trifluoromethyl-$C_7$ to $C_{12}$ alkyl radical:
 4,6-dithia-5-[2-(12,12,12-trifluorododecyl)phenyl]-nonanedioic acid;

(G) where $R_3$ is a

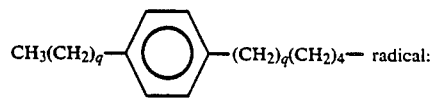 radical:

4,6-dithia-5-[2-(4-(4-butylphenyl)butyl)phenyl]-nonanedioic acid;

(H) where $R_3$ is 11-dodecynyl:
 4,6-dithia-5-[2-(11-dodecynyl)phenyl]nonanedioic acid;

(I) where $R_3$ is 1-trans-dodecenyl:
 4,6-dithia-5-[2-(1-trans-dodecenyl)phenyl]nonanedioic acid;

(J) where $R_3$ is 5-(4-acetyl-3-hydroxy-2-propyl-phenoxy)-pentoxy;
 4,6-dithia-5-[2-(5-(4-acetyl-3-hydroxy-2-propyl-phenoxy)-pentoxy)phenyl]nonanedioic acid; and (K) where $R_3$ is phenyl—CH=CH—$(CH_2)_{2-8}$:
 4,6-dithia-5-[2-(8-phenyl-7(Z)-octenyl)phenyl]-nonanedioic acid.

The compounds of the formula (III) wherein $R_4$ is bromo, chloro, methyl, trifluoromethyl, hydroxy, methoxy or nitro are exemplified by the following compounds:

(A) 4,6-dithia-5-(5-methoxy-2-undecyloxyphenyl)-nonanedioic acid;
(B) 4,6-dithia-5-(5-bromo-2-undecyloxyphenyl)-nonanedioic acid;
(C) 4,6-dithia-5-(5-nitro-2-undecyloxyphenyl)-nonanedioic acid;
(D) 4,6-dithia-5-(5-hydroxy-2-undecyloxyphenyl)-nonanedioic acid; and
(E) 4,6-dithia-5-[2-(8-phenyloctyl)-5-trifluoromethylphenyl]nonanedioic acid.

Additional illustrations of the compounds of formula (II) are the 3,5-dithiaheptanedioic acid derivatives where both m and n are 1; 4,6-dithiadecanedioic acid derivatives where m is 2 and n is 3; and the 3,5-dithiaoctanedioic acid derivatives where m is 1 and n is 2. The 3,5-dithiaheptanedioic acid derivatives of formula (II) are exemplified by 3,5-dithia-4-(2-dodecylphenyl)heptanedioic acid.

Additional members of this first class of compounds are those represented by the structural formula (II) wherein $R_1$ is hydrogen; $R_2$ is selected from the group consisting of $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecynyl, 1-trans-dodecenyl, 5-(4-acetyl-3-hydroxy-2-propylphenoxy)-pentoxy, 2(Z),5(Z)-undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl —CH=CH—$(CH_2)_{2-8}$, phenyl-$C_3$ to $C_9$ alkoxy, trifluoromethyl-$C_7$ to $C_{12}$ alkyl, cyclohexyl-$C_4$ to $C_{10}$ alkyl, and

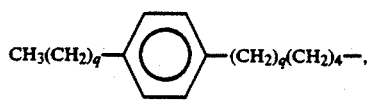

and m, n and q are described above.

A subgeneric class of these compounds are the 4,6-dithianonanedioic acid derivatives represented by the following general structural formula (IV)

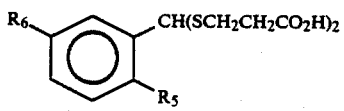

wherein $R_5$ is hydrogen and $R_6$ is selected from the group consisting of $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecynyl, 1-trans-dodecenyl, 5-(4-acetyl-3-hydroxy-2-propylphenoxy)-pentoxy, 2(Z),5(Z)-undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl —CH=CH—$(CH_2)_{2-8}$, phenyl-$C_3$ to $C_9$ alkoxy, trifluoromethyl-$C_7$ to $C_{12}$ alkyl, cyclohexyl-$C_4$ to $C_{10}$ alkyl, and

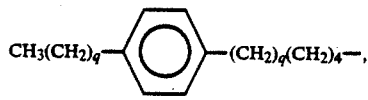

and q is described above.

The compounds of formula (IV) wherein $R_5$ is hydrogen are exemplified by the following compounds in which $R_6$ is an alkoxy radical containing from 7 to 12 carbon atoms:

(A) 4,6-dithia-5-(3-undecyloxyphenyl)nonanedioic acid; and (B) 4,6-dithia-5-(3-nonyloxyphenyl)nonanedioic acid.

The compounds of the formula (IV) are also exemplified by 4,6-dithia-5-[3-(2(Z),5(Z)-undecadienyloxy)phenyl]nonanedioic acid and 4,6-dithia-5-[3-(8-phenyloctyl)phenyl]nonanedioic acid.

A second class of compounds of this invention are the substituted thienyldioic acid analogs of the formula (I) wherein R' is hydrogen and R is the thienyl radical and are represented by the structural formula (V)

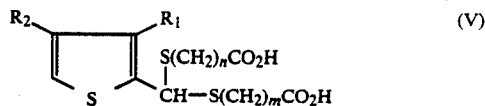

wherein m, n, $R_1$ and $R_2$ are described above. Exemplifying this second class of compounds are 4,6-dithia-5-(3-dodecyl-2-thienyl)nonanedioic acid [formula (V) where m and n are both 2, $R_1$ is dodecyl and $R_2$ is hydrogen] and 4,6-dithia-5-(4-dodecyl-2-thienyl)nonanedioic acid [formula (V) where m and n are both 2, $R_1$ is hydrogen and $R_2$ is dodecyl].

Another class of compounds of this invention are the compounds of the formula (I) wherein R' is methyl. Exemplifying this class of compounds is 4,6-dithia-5-methyl-5-(2-undecyloxyphenyl)nonanedioic acid [formula I wherein m and n are both 2, R' is methyl and R is 2-undecyloxyphenyl].

A further class of compounds of this invention are the compounds of the formula (I) wherein p is 1. Exemplifying this class of compounds is 5-(2-dodecylphenyl)-4-sulfinyl-6-thianonanedioic acid [formula I wherein m and n are both 2, R' is hydrogen, R is 2-dodecylphenyl and p is 1].

The compounds of the present invention are acidic and are, therefore, capable of forming salts with pharmaceutically acceptable bases according to procedures well known in the art. Such acceptable bases include organic and inorganic bases, such as ammonia, organic amines and alkali metal bases.

The compounds of the formula (I) wherein p is 0 are conveniently prepared by forming the dithioacetal derivatives or dithioketal derivatives of the aldehydes or ketones, respectively, of the following structural formula (VI)

$$RR'CO \qquad (VI)$$

wherein R and R' are described above, utilizing the appropriate mercaptoalkanoic acids. The reaction of the compound of formula (VI) with two equivalents of the mercaptoalkanoic acid is accomplished at low to moderate temperatures under acidic conditions in an inert solvent or excess of the mercaptoalkanoic acid. Examples of such inert solvents include chlorinated hydrocarbons, such as methylene chloride, chloroform and dichloroethane. The acidic conditions are produced by mineral acids, such as hydrochloric acid and sulfuric acid, or Lewis acids, such as boron trifluoride etherate. The reaction temperatures can range from −40° C. to ambient temperatures.

The compounds of the formulae (III) and (IV) wherein p is 0 are prepared by reacting 3-mercaptopropionic acid with the appropriate aldehyde of the formula (VI). Similarly, employing mercaptoacetic acid, the compounds of the formula (I) wherein both m and n are 1 and p is 0 can be prepared. To prepare the compounds of formula (I) wherein m is not equal to n and p is 0, a mixture of the appropriate mercaptoalkanoic acids is employed followed by separation and isolation of the desired compounds.

To prepare the compounds of formula (I) wherein p is 1, the appropriate dithia acid product is conveniently oxidized with either metachloroperbenzoic acid or, when $R_1$ or $R_2$ contains unsaturation, sodium periodate, using one equivalent of either oxidant.

The aldehydes and ketones of the formula (VI) are known or readily prepared utilizing the general procedures described as follows.

The aldehyde precursors to the compounds of the formula (II) wherein $R_1$ is, for example, an alkyl radical containing 8 to 13 carbon atoms are prepared from the appropriate 2-methoxyphenyl-4,4-dimethyloxazoline [see Meyers et al. *J. Org. Chem.*, 43 1372 (1978)].

The aldehyde precursors of the compounds of the formula (II) wherein $R_1$ or $R_2$ is, for example, an alkoxy radical containing 7 to 12 carbon atoms or a 2(Z),5(Z)-undecadienyloxy radical are prepared by the O-alkylation of the appropriate 2 or 3 hydroxybenzaldehyde with the corresponding alkylating agent.

The aldehyde precursors to the compounds of the formula (II) wherein $R_1$ or $R_2$ is a 1-alkynyl radical containing 10 to 12 carbon atoms are prepared by coupling a 2 or 3 substituted halobenzaldehyde with the appropriate 1-alkyne in the presence of cuprous iodide and $(P\phi_3)_2PdCl_2$. [See Hagihara, et al. *Synthesis*, 627, (1980)]. The catalytic hydrogenation of these alkynyl containing precursors under standard conditions affords the aldehyde precursors of the compounds of the formula (II) wherein $R_1$ or $R_2$ is an alkyl or phenylalkyl radical.

The aldehyde precursors to the compounds of the formula (V) wherein $R_1$ or $R_2$ is an alkyl radical containing 8 to 13 carbon atoms are prepared by the carbonylation of the appropriate 3-alkylthiophene with phosphory chloride/dimethylformamide.

The thioalkyl containing aldehyde precursors of the compounds of the formula (II) are prepared by the reaction of the appropriately substituted halothioalkylbenzene with magnesium and dimethylformamide.

The phenylthioalkyl containing aldehyde precursors of the compounds of the formula (II) are prepared by the reaction of the appropriately substituted haloalkyl benzoic acid with a thiophenol and triethylamine, followed by reduction with lithium aluminum hydride to the benzyl alcohol and oxidation with manganese dioxide to the desired aldehyde.

The leukotriene antagonist activity of the compounds of this invention is measured by the ability of the compounds to inhibit the leukotriene induced contraction of guinea pig tracheal tissues in vitro and to inhibit leukotriene induced bronchoconstriction in guinea pigs in vivo. The following methodologies were employed: In vitro: Guinea pig (adult male albino Hartley strain) tracheal spiral strips of approximate dimensions 2 to 3 mm cross-sectional width and 3.5 cm length were bathed in modified Krebs buffer in jacketed 10 ml tissue bath and continously aerated with 95% $O_2$/5% $CO_2$. The tissues were connected via silk suture to force displacement transducers for recording isometric tension. The tissues were equilibrated for 1 hr., pretreated for 15 minutes with meclofenamic acid (1 $\mu M$) to remove intrinsic prostaglandin responses, and then pretreated for an additional 30 minutes with either the test compound or vehicle control. A cumulative concentration-response curve for $LTD_4$ on triplicate tissues was generated by successive increases in the bath concentration of the $LTD_4$. In order to minimize intertissue variability, the contractions elicited by $LTD_4$ were standardized as a percentage of the maximum response obtained to a reference agonist, carbachol (10 $\mu M$).

Calculations: The averages of the triplicate $LTD_4$ concentration-response curves both in the presence and absence of the test compound were plotted on log graph paper. The concentration of $LTD_4$ needed to elicit 30% of the contraction elicited by carbachol was measured and defined as the $EC_{30}$. The $-\log K_B$ value for the test compound was determined by the following equations:

$$\frac{EC_{30} \text{ (presence of test compound)}}{EC_{30} \text{ (presence of vehicle control)}} = \text{dose ratio} = X \qquad 1.$$

$$K_B = \text{concentration of test compound}/(X - 1) \qquad 2.$$

In vivo: Anesthetized, spontaneously breathing guinea pigs (Adult male albino Hartley strain) were monitored on a Buxco pulmonary mechanics computer. Changes in airway resistance ($R_L$) were calculated by the computer on a breath-by-breath basis at isovolumic points from signals measuring airflow and transpulmonary pressure using differential pressure transducers. Animals received either test compound or vehicle control intravenously via the jugular vein. $LTD_4$ was then injected into the jugular vein. The bronchoconstriction produced was reflected by % changes in airways resistance relative to the baseline values obtained prior to injection of the test compound or vehicle control. Each guinea pig received either vehicle control or test compound.

Calculations: The average of 3-6 animals per treatment was calculated using the % changes in the pulmonary parameters for control and test compound-treated animals. The average % inhibition by the test compound was calculated from the following equation:

$$\% \text{ Inhibition} = \frac{R_L \text{ (vehicle control)} - R_L \text{ (test compound)}}{R_L \text{ (vehicle control)}} \times 100$$

The compounds of this invention possess biosignificant antagonist activity against leukotrienes, primarily leukotriene $D_4$. The antagonist activity of representative compunds of this invention is tabulated below. The $-\log K_B$ values and the $R_L$ values were calculated from the above test protocols.

|   |   |   |   | In Vitro | In Vivo | |
|---|---|---|---|---|---|---|
| m | n | $R_1$ | $R_2$ | $-\text{Log } K_B$ | Concentration (mg/kg) | % Inhibition of $R_L$ |
| Compounds of the Formula (II) | | | | | | |
| 2 | 2 | $-C_{12}H_{25}$ | H | 6.2 | 5 | 96.5 |
| 2 | 2 | $-C_{10}H_{21}$ | H | 6.5 | 5 | 60.7 |
| 2 | 2 | $-C_8H_{17}$ | H | 5.2 | — | — |
| 2 | 2 | $-OC_{11}H_{23}$ | H | 6.4 | 10 | 89.4 |
| 2 | 2 | $-OC_9H_{19}$ | H | 5.8 | | |
| 2 | 2 | $-OCH_2-CH=CHCH_2-CH=CHC_5H_{11}$ | H | 6.0 | — | |

-continued

| m | n | $R_1$ | $R_2$ | In Vitro $-\text{Log } K_B$ | In Vivo Concentration (mg/kg) | % Inhibition of $R_L$ |
|---|---|---|---|---|---|---|
| 2 | 2 | $-OC_{11}H_{23}$ | $CH_3O$ | 5.9 | — | |
| 2 | 2 | $-OC_{11}H_{23}$ | Br | 6.0 | — | |
| 2 | 2 | $-OC_{11}H_{23}$ | $NO_2$ | 6.1 | — | |
| 2 | 2 | $-SC_{11}H_{23}$ | H | 6.0 | — | |
| 2 | 2 | $-C\equiv C-C_{10}H_{21}$ | H | 6.1 | — | |
| 1 | 1 | $-C_{12}H_{25}$ | H | 5.9 | — | |
| 2 | 2 | $-OC_6H_{12}$phenyl | H | 5.3 | 10 | 26.4 |
| 2 | 2 | $-C_8H_{16}$phenyl | H | 6.5 | (1)5 | 100 |
|   |   |   |   |   | (2)5 | 95.3 |
| 2 | 2 | $-C_{11}H_{22}CF_3$ | H | 6.2 | 5 | 30.4 |
| 2 | 2 | $-C_8H_{16}$cyclohexyl | H | 5.5 | — | |
| 2 | 2 | $-(CH_2)_4-\text{phenyl}-C_4H_9$ | H | 5.6 | — | |
| 2 | 2 | $-CH\equiv CH-C_{10}H_{21}$ trans | H | 5.8 | — | |
| 2 | 2 | $-OC_{11}H_{23}$ | OH | 6.0 | — | |
| 2 | 2 | $-C_{10}H_{20}C\equiv CH$ | H | 6.4 | — | |
| 2 | 2 | $-C_8H_{16}$phenyl | $CF_3$ | 6.6 | — | |
| 2 | 2 | $-OC_5H_{10}$(4-acetyl-3-hydroxy-2-propylphenoxy) | H | 6.6 | — | |
| 2 | 2 | $-(CH_2)_6-CH\equiv CH-\text{phenyl}$ | H | 6.2 | — | |
| 2 | 2 | $-C_7H_4S$ phenyl | H | 6.4 | — | |
| 2 | 2 | $-C_8H_{16}-(4-CF_3\text{phenyl})$ | H | 6.2 | — | |
| 2 | 2 | H | $-OC_{11}H_{23}$ | 6.1 | | |
| 2 | 2 | H | $-OC_9H_{19}$ | 5.9 | | |
| 2 | 2 | H | $-OCH_2CH\equiv CHCH_2CH\equiv CHC_5H_{11}$ | 6.1 | | |
| 2 | 2 | H | $-C_8H_{16}$phenyl | 6.0 | | |
| Compounds of the Formula (V) | | | | | | |
| 2 | 2 | $C_{12}H_{25}$ | H | 5.9 | | |
| 2 | 2 | H | $C_{12}H_{25}$ | 5.5 | | |

The compound 4,6-dithia-5-methyl-5-(2-undecyloxyphenyl)nonanedioic acid exhibited a $-\log K_B$ of 5.3 and the compound 5-(2-dodecylphenyl)-4-sulfinyl-6-thianonanedioic acid exhibited a $-\log K_B$ of 5.8.

The specificity of the antagonist activity of a number of the compounds of this invention is demonstrated by relatively low levels of antagonism toward agonists such as potassium chloride, carbachol, histamine and $PGF_{2\alpha}$.

A compound of this invention, namely 4,6-dithia-5-[2-(8-phenyloctyl)phenyl]nonanedioic acid, demonstrated anti-inflammatory activity against arachidonic acid-induced inflammation in mice upon topical, subcutaneous and oral administration (oral $ED_{50}$=104.8 mg/kg). This compound also demonstrated activity against carrageenan peritonitis in mice following oral administration at 100 mg/kg. These results suggest that this compound may also antagonize $LTB_4$ or that it inhibits lipoxygenase activity.

Pharmaceutical compositions of the present invention comprise a pharmaceutical carrier or diluent and an amount of a compound of the formula (I) or a pharmaceutically acceptable salt, such as an alkali metal salt thereof sufficient to produce the inhibition of the effects of leukotrienes, such as symptoms of asthma and other hypersensitivity diseases.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will, of course, depend upon the intended route of administration, i.e. parenterally, topically or by inhalation.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

For parenteral administration the pharmaceutical composition will be in the form of a sterile injectable liquid such as an ampul or an aqueous or nonaqueous liquid suspension.

For topical administration the pharmaceutical composition will be in the form of a cream or ointment.

Usually a compound of formula I is administered to an animal subject in a composition comprising a nontoxic amount sufficient to produce an inhibition of the symptoms of an allergic response. When employed in this manner, the dosage of the composition is selected from the range of from 350 mg. to 700 mg. of active ingredient for each administration. For convenience, equal doses will be administered 1 to 4 times daily with the daily dosage regimen being selected from about 350 mg. to about 2800 mg.

The pharmaceutical preparations thus described are made following the conventional techniques of the pharmaceutical chemist as appropriate to the desired end product.

Included within the scope of this disclosure is the method of inhibiting the symptoms of an allergic response resulting from a mediator release which comprises administering to an animal subject a therapeutically effective amount for producing said inhibition of a compound of formula I, preferably in the form of a pharmaceutical composition. The administration may be carried out in dosage units at suitable intervals or in single doses as needed. Usually this method will be practiced when relief of allergic symptoms is specifically required. However, the method is also usefully carried out as continuous or prophylactic treatment. It is within the skill of the art to determine by routine experimentation the effective dosage to be administered from the dose range set forth above, taking into consideration such factors as the degree of severity of the allergic condition being treated, and so forth.

The following examples illustrate the preparation of the compounds of this invention and their incorporation into pharmaceutical compositions and as such are not to be considered as limiting the invention set forth in the claims appended hereto.

EXAMPLE 1

Preparation of 4,6-Dithia-5-(2-dodecylphenyl) nonanedioic acid (a) 2-(2-Dodecylphenyl)-4,4-dimethyloxazoline To freshly prepared dodecylmagnesium bromide (from 30.13 mmoles of dodecyl bromide and 26.20 mmoles of magnesium) in distilled tetrahydrofuran (50 ml) was added 2-(2-methoxyphenyl)-4,4-dimethyloxazoline [A. I. Meyers et al., *J. Org. Chem.*, 43, 1372 (1978)] (17.88 mmoles) in tetrahydrofuran (30 ml). The resultant yellow solution was stirred under argon at ambient temperature for 20 hours. The solution was cooled in an ice water bath and quenched with aqueous ammonium chloride (100 ml). The reaction product was extracted into diethyl ether (100 ml) and the organic phase was washed with saturated sodium chloride solution (50 ml) and then dried over anhydrous magnesium sulfate. Evaporation of the organic phase afforded a colorless oil which was purified by flash chromatography over silica gel with 5 percent ethyl acetate in hexane as eluant to afford the desired product as a pale yellow oil.

Analysis for $C_{23}H_{37}NO$: Calculated: C, 80.41; H, 10.85; N, 4.08. Found: C, 80.22; H, 10.56; N, 3.87.

(b) 2-(2-Dodecylphenyl)-3,4,4-trimethyloxazolinium iodide

A solution of the compound of Example 1(a) (17.2 mmoles) in methyl iodide (20 ml) was refluxed under argon for 18 hours. The volatiles were removed under vacuum and the solid residue triturated with ethyl acetate (25 ml) to afford the desired product as white crystals (mp 78°–84° C.).

(c) 2-Dodecylbenzaldehye

To an ice cold solution of the compound of Example 1(b) (10.0 mmoles) in methanol (50 ml) over a period of 15 minutes was added in small portions sodium borohydride (10.0 mmoles). The reaction mixture was allowed to stir for 30 minutes and was then quenched with 5 percent sodium hydroxide (50 ml). The reaction mixture was extracted with diethyl ether (2×50 ml) and the extract was washed with brine (50 ml) and dried over anhydrous magnesium sulfate. Evaporation of the extract afforded an oil which was dissolved in acetone (50 ml) and 3 N hydrochloric acid (10 ml) was added. The mixture was flushed with argon and stirred for 16 hours at ambient temperature. The volatiles were removed under vacuum and the residue partitioned between diethyl ether (50 ml) and water (50 ml). The aqueous phase was extracted with more diethyl ether (50 ml). The combined organic phase was washed with brine (50 ml) and dried over anhydrous magnesium sulfate. Evaporation of the organic phase yielded an oil which was purified by flash chromatography over silica gel with 2 percent ethyl acetate in hexane as eluant to afford the desired product as a colorless oil. Analysis for $C_{19}H_{30}O$: Calculated: C, 83.15; H, 11.02. Found C, 82.59; H, 10.65.

(d) 4,6-Dithia-5-(2-dodecylphenyl)nonanedioic acid

To an ice cold solution of the compound of Example 1(c) (4.23 mmoles) and 3-mercaptopropionic acid (9.3 mmoles) in methylene chloride (25 ml) was added dropwise distilled boron trifluoride etherate (4.23 mmoles). After 15 minutes, the mixture was taken up in diethylether (100 ml) and washed with water (5×100 ml). The organic phase was dried over anhydrous magnesium sulfate and after removal of the volatiles under vacuum, the resultant colorless oil was stored under argon in a freezer. It slowly crystallized to afford the desired product as a white solid (mp 34°–38° C.). Analysis for $C_{25}H_{40}O_4S_2$: Calculated: C, 64.06; H, 8.60; S, 13.68. Found C, 64.19; H, 8.47; S, 13.63.

The following compounds were prepared according to the general method described above from the 2-(2-methoxyphenyl)-4,4-dimethyloxazoline and the appropriate alkyl halide:

4,6-dithia-5-(2-decylphenyl)nonanedioic acid (mp 66°–69.5° C.);

4,6-dithia-5-(2-octylphenyl)nonanedioic acid (mp 61°–64° C.); and 3,5-dithia-4-(2-dodecylphenyl)heptanedioic acid (mp 80°–81.5° C.).

Similarly, the following compounds of the formula (II) are prepared utilizing the general method of Example 1 from the appropriate reactants:

| m | n | $R_1$ | $R_2$ |
|---|---|-------|-------|
| 1 | 1 | $C_{10}H_{21}$ | Br |
| 1 | 1 | $C_8H_{17}$ | $OCH_3$ |

EXAMPLE 2

Preparation of 4,6-Dithia-5-(2-undecyloxyphenyl) nonanedioic acid (a) 2-undecyloxybenzaldehyde To a stirred suspension of sodium hydride (10.0 mmoles), which was prewashed with petroleum ether, in sieve dried dimethylformamide (10 ml) was added dropwise a solution of salicylaldehyde (10.1 mmoles) in dimethylformamide (1 ml). To the reaction mixture was then added undecyl bromide (10.0 mmoles) and the mixture stirred for 16 hours at ambient temperature under nitrogen. The reaction mixture was taken up in hexane (50 ml) and washed with 10 percent sodium hydroxide (2×50 ml) and saturated sodium chloride (50 ml). The organic phase was dried over anhydrous magnesium sulfate and charcoal. Evaporation of the volatiles yielded a colorless liquid which was purified by flash chromatography over silica gel with 2 percent ethyl acetate in hexane as eluant to afford the desired product as an oil.

Analysis for $C_{18}H_{28}O_2$: Calculated: C, 78.21; H, 10.21. Found: C, 77.92; H, 9.95.

(b) 4,6-Dithia-5-(2-undecyloxyphenyl)nonanedioic acid

Employing the general method of Example 1(d), the compound of Example 2(a) (3.62 mmoles) was reacted with 3-mercaptopropionic acid (8.03 mmoles) to yield the desired product as a white crystalline solid (mp 76-°78.5° C.).

Analysis for $C_{24}H_{38}O_5S_2$: Calculated: C, 61.24; H, 8.14; S, 13.62. Found: C, 61.56; H, 8.08; S, 13.51.

The following compounds were prepared according to the general method described above from the appropriately substituted hydroxybenzaldehyde and the appropriate alkyl halide.

4,6-dithia-5-(2-nonyloxyphenyl)nonanedioic acid (mp. 76°-78.5° C.);

4,6-dithia-5[2-(2(Z),5(Z)-undecadienyloxy)phenyl]-nonanedioic acid (oil);

4,6-dithia-5-(5-methoxy-2-undecyloxyphenyl)-nonanedioic acid (mp 55°-57° C.);

4,6-dithia-5-(5-bromo-2-undecyloxyphenyl)nonanedioic acid (mp 79°-81° C.);

4,6-dithia-5-(5-nitro-2-undecyloxyphenyl)nonanedioic acid (mp 99°-101° C.);

4,6-dithia-5-(5-hydroxy-2-undecyloxyphenyl)-nonanedioic acid (mp 102°-105° C.);

4,6-dithia-5-(3-undecyloxyphenyl)nonanedioic acid (mp 59°-60.5° C.);

4,6-dithia-5-(3-nonyloxyphenyl)nonanedioic acid (mp 78°-79° C.) and 4,6-dithia-5-[3-(2(Z),5(Z)-undecadienyloxy)phenyl]-nonanedioic acid (oil).

4,6-Dithia-5-(2-undecylthiophenyl)nonanedioic acid [formula (III) where $R_3$ is $-SC_{11}H_{23}$ and $R_4$ is H] was prepared from 2-(undecylthio)benzaldehyde and was obtained in the form of an oil.

Analysis for $C_{24}H_{38}O_4S_3$: Calculated: C, 59.22; H, 7.87; S, 19.76. Found: C, 58.90, H, 7.91; S, 19.06, 18.92.

The following compound of the formula (I) wherein R' is methyl was prepared according to the general method described above from the appropriate substituted alkoxyacetophenone:

b   4,6-dithia-5-methyl-5-(2-undecyloxyphenyl)-nonanedioic acid (amorphous solid).

Analysis for $C_{25}H_{40}O_5S_2$: Calculated: C, 61.95; H, 8.32. Found: C, 61.15; H, 8.22.

Similarly, the following compounds of the formula (II) are prepared utilizing the general method of Example 2 from the appropriate reactants.

| m | n | $R_1$ | $R_2$ |
|---|---|---|---|
| 1 | 1 | $OC_{11}H_{23}$ | H |
| 1 | 1 | $OC_9H_{19}$ | Br |
| 1 | 1 | H | $OC_{11}H_{23}$ |

EXAMPLE 3

Alternate Preparation of Alkoxybenzaldehyde Intermediates (a) 2-Undecyloxybenzaldehyde A mixture of salicylaldehyde (10.15 moles), undecylbromide (10.3 mmoles) and potassium carbonate (11.7 mmoles) in dimethylformamide (10 ml) is heated to 100° C. for 1 hour and then is cooled. The reaction mixture is taken up in hexane and is washed with 5 percent sodium hydroxide and brine. After treatment with anhydrous magnesium sulfate and charcoal, the volatiles are removed under vacuum and the residue is purified by flash chromatography to give the desired product.

EXAMPLE 4

Preparation of 4,6-Dithia-5-[2-(1-dodecyn-1-yl)phenyl]nonanedioic acid (a) 2-(1-dodecyn-1-yl)benzaldehyde A mixture of 2-bromobenzaldehyde (10.05 mmoles), 1-dodecyne (12.03 mmoles), cuprous iodide (0.11 mmoles) and bis(triphenylphosphine) palladium chloride (0.20 mmoles) in freshly distilled triethylamine (30 ml.) was heated for one hour at reflux producing a white precipitate. The reaction mixture was cooled and filtered. The filtrate was evaporated to dryness at reduced pressure and then dissolved in diethyl ether (50 ml) and washed with brine (50 ml). After treatment with anhydrous magnesium sulfate and charcoal, the solution was evaporated to afford a dark oil, which was purified by flash chromatography (2% $Et_2O$/hexane) to yield the desired product.

(b) 4,6-Dithia-5-[2-(1-dodecyn-1-yl)phenyl]nonanedioic acid

Employing the general method of Example 1(d), the compound of Example 4(a) (2.26 mmoles) was reacted with mercaptopropionic acid (4.93 mmoles) to yield the desired product as a pale yellow liquid.

Analysis for $C_{25}H_{36}O_4S_2$: Calculated: C, 64.62; H, 7.81; S, 13.80. Found: C, 63.90; H, 7.72; S, 13.76.

EXAMPLE 5

Preparation of 4,6-Dithia-5-(4-dodecyl-2-thienyl) nonanedioic acid (a) 3-Dodecylthiophene To a freshly prepared dodecylmagnesium bromide (from 45 mmoles of dodecyl bromide and 45 mmoles of magnesium) in anhydrous diethyl ether (100 ml) was added 3-bromothiophene (45 mmoles) in diethyl ether (25 ml) at ambient temperature under argon and then bis-(1,2-diphenylphosphino)ethane nickel (II) chloride (0.25 g) was added. The reaction mixture was stirred overnight at ambient temperature and then hydrolyzed with ice and saturated aqueous ammonium chloride. The aqueous layer was extracted with diethyl ether (3×25 ml) and the organic phases were combined, washed with water (3×25 ml), dried over anhydrous magnesium sulfate and concentrated in vacuo. The crude product was purified by distillation in vacuo and then flash chromatography to afford the desired product.

(b) 3-Dodecyl-2-thiophenecarboxaldehyde [5(b)(1)] and 4-Dodecyl-2-thiophenecarboxaldehyde [5(b)(2)]

To a cold solution of phosphoryl chloride (30.3 mmoles) and N,N-dimethylformamide (30.3 mmoles) was added the compound of Example 5(a) (20.2 mmoles) in dimethylformamide (20 ml) under argon with stirring. The mixture was allowed to warm to ambient temperature and then heated at 60° C. overnight. The reaction mixture was poured into ice-water (75 ml) and then extracted with diethyl ether (3×25 ml). The ether extracts were combined, washed with water (3×25 ml), dried over anhydrous magnesium sulfate and concentrated to give a crude mixture of Compounds 5(b)(1) and 5(b)(2) which were purified by preparative high pressure liquid chromatography.

(c) 4,6-Dithia-5-(4-dodecyl-2-thienyl)nonanedioic acid

Employing the general method of Example 1(d), Compound 5(b)(2) (4.6 mmoles) was reacted with 3-mercaptopropionic acid (10.7 mmoles) to yield the desired product, a white crystalline solid (mp 90°-92° C.).

Analysis for $C_{23}H_{38}O_4S_3$: Calculated: C, 58.19; H, 8.06. Found: C, 58.16; H, 8.04.

Similarly, 4,6-dithia-5-(3-dodecyl-2-thienyl)-nonanedioic acid (mp 61°-62° C.) was prepared from Compound 5(b)(1).

Analysis for $C_{23}H_{38}O_4S_3$: Calculated: C, 58.19; H, 8.06. Found: C, 57.90; H, 8.03.

EXAMPLE 6

Preparation of 4,6-Dithia-5-[2-(6-phenylhexyloxy)phenyl]nonanedioic acid (a) 2-(6-Phenylhexyloxy)benzaldehyde A solution of 6-phenylhexanoic acid (19.8 mmoles) in sieve dried tetrahydrofuran (5 ml) was reduced with diborane in tetrahydrofuran (30 ml, 29.1 mmoles) at 0° C. for 4 hours to give 6-phenylhexanol. To an ice cold solution of the hexanol (ca. 19.8 mmoles) and carbon tetrabromide (21.98 mmoles) in methylene chloride (50 ml) was added triphenylphosphine (22.30 mmoles) in methylene chloride (50 ml) and the resulting solution was stirred for 2.5 hours. The volatiles were evaporated and the residue was taken up in ether (100 ml), cooled in ice, and filtered The filtrate was evaporated and distilled to afford 6-phenylhexyl bromide as an oil. A mixture of the bromide (8.00 mmoles), salicylaldehyde (8.19 mmoles) and potassium carbonate (9.33 mmoles) in dimethylformamide (10 ml) was heated to 100° C. and maintained at that temperature for one hour. The cooled reaction mixture was taken up in hexane (50 ml) and washed with 5% sodium hydroxide (50 ml) and saturated sodium chloride (50 ml). The organic phase was dried over anhydrous magnesium sulfate and charcoal. Evaporation yielded a colorless oil which was purified by flash chromatography over silica gel with 5% ethyl acetate in hexane as eluant to afford the desired product as an oil.

Analysis for $C_{19}H_{22}O_2$: Calculated: C, 80.82; H, 7.85. Found: C, 80.62; H, 7.72.

(b) 4,6-Dithia-5-[2-(6-phenylhexyloxy)phenyl]-nonanedioic acid

Employing the general method of Example 1(d), the compound of Example 6(a) (5.35 mmoles) was reacted with 3-mercaptopropionic acid (11.47 mmoles) to yield the desired product as a white solid (mp 71°-74° C.).

Analysis for $C_{25}H_{32}O_5S_2$: Calculated: C, 63.00; H, 6.77; S, 13.45. Found: C, 62.88; H, 6.74; S, 13.40.

EXAMPLE 7

Preparation of 4,6-Dithia-5-[2-(8-phenyloctyl)phenyl]nonanedioic acid (a) 2-(8-Phenyloctyl)benzaldehyde Following the procedures of Example 1(a), (b) and (c), to 8-phenyloctylmagnesium bromide (from 24.25 mmoles of 8-phenyloctyl bromide and 21.27 mmoles of magnesium) in distilled tetrahydrofuran (40 ml) was added 2-(2-methoxyphenyl)-4,4-dimethyloxazoline (17.10 mmoles) in tetrahydrofuran (20 ml). [The 8-phenyloctyl bromide was prepared from 8-phenyloctanol, carbon tetrabromide and triphenylphosphine in methylene chloride as described in Example 6(a).] After stirring for 24 hours, the reaction mixture was similarly worked up to yield 2-[2-(8-phenyloctyl)phenyl]-4,4-dimethyloxazoline as an oil. A solution of the oxazoline (11.58 mmoles) in methyl iodide (20 ml) was refluxed under argon for 18 hours. Removal of the volatiles afforded the corresponding 3,4,4-trimethyloxazolinium iodide as a white solid (mp 76.5°-78° C.). To an ice cold solution of the iodide (9.46 mmoles) in methanol (35 ml) was added in portions sodium borohydride (9.20 mmoles). Treatment of the reaction mixture as in Example 1(c) results in the isolation of the desired product as an oil.

Analysis for $C_{21}H_{26}O$: Calculated: C, 85.67; H, 8.90. Found: C, 85.12, 85.22; H, 8.94, 8.96.

(b) Alternative preparation of 2-(8-phenyloctyl)benzaldehyde

A solution of 5-hexynyl alcohol (102 mmoles) in pyridine (150 ml), under argon, was cooled to 0° C. and p-toluenesulfonyl chloride (204 mmoles) was added. The reaction mixture was kept at about 4° C. for 18 hours, poured into ice-water and then taken up in ether. The ether extract was washed with cold 10% hydrochloric acid, water and brine. The organic layer was dried and concentrated in vacuo to give 5-hexynyl p-toluenesulfonate. A solution of phenylacetylene (97 mmoles) in tetrahydrofuran (200 ml) containing a trace of triphenylmethane was cooled to 0° C. and then n-butyl lithium (37.3 ml of 2.6 moles in hexane) was added dropwise. The resulting solution was stirred at 0° C. for 10 minutes and hexamethylphosphoramide (21 ml) was added dropwise. After stirring for 10 minutes a solution of 5-hexynyl p-toluenesulfonate (97.1 mmoles) in tetrahydrofuran (200 ml) was added. The reaction mixture was stirred for 18 hours, diluted with ether and the organic layer was washed with water and brine. The dried organic solution was concentrated and the product was purified by flash chromatography to give 1-phenylocta-1,7-diyne. A mixture of this compound (43 mmoles), 2-bromobenzaldehyde (35.8 mmoles), cuprous iodide (0.5 mmoles) and bis(triphenylphosphine) palladium chloride (0.7 mmoles) in triethylamine (100 ml) was heated in an oil bath (95° C.) for one hour. The reaction mixture was cooled to 0° C., filtered and the filtrate was concentrated. The residue was dissolved in ether, washed with 10% hydrochloric acid, water and brine. The organic layer was dried and concentrated to give a product which was purified by flash chromatography to yield 2-(8-phenyloctadiyn-1,7-yl)benzaldehyde. A solution of this compound (24.1 mmoles) in ethyl acetate (100 ml) and 10% palladium on charcoal (1 g) was hydrogenated (40 psi of hydrogen) at room temperature for 15 minutes. The catalyst was filtered off and the filtrate concentrated to give the 2-(8-phenyloctyl)benzaldehyde.

(c) 4,6-Dithia-5-[2-(8-phenyloctyl)phenyl]nonanedioic acid

To an ice cold solution of the aldehyde from Example 7(a) or 7(b) (5.94 mmoles) and 3-mercaptopropionic acid (12.97 mmoles) in methylene chloride (32 ml) was added dropwise boron trifluoride etherate (5.94 mmoles). After 15 minutes the reaction mixture was diluted with ether (100 ml) and washed with water (5×100 ml). The organic phase was dried over anhydrous magnesium sulfate and charcoal. Evaporation of the volatiles yielded an oil which crystallized to the desired product as a white solid (mp 56°–59° C.).

Analysis for $C_{27}H_{36}O_4S_2$: Calculated: C, 66.36; H, 7.42; S, 13.12. Found: C, 66.16; H, 7.34; S, 13.16.

EXAMPLE 8

Preparation of 4,6-Dithia-5-[2-(12,12,12-trifluorododecyl)phenyl]-nonanedioic acid (a) 2-(12,12,12-Trifluorododecyl)benzaldehyde Following the procedures of Example 1(a), (b) and (c), 12,12,12-trifluorododecylmagnesium bromide (from 29.19 mmoles of 12,12,12-trifluorododecyl bromide and 25.71 mmoles of magnesium) was reacted with 2-(2-methoxyphenyl)-4,4-dimethyloxazoline (20.17 mmoles) in tetrahydrofuran to give 2-[2-(12,12,12-trifluorododecyl)phenyl]-4,4-dimethyloxazoline. The oxazoline (14.39 mmoles) was converted to the methiodide salt and then reduced with sodium borohydride (13.43 mmoles) to yield the desired product as an oil.

Analysis for $C_{19}H_{27}F_3O$: Calculated: C, 69.49; H, 8.29. Found: C, 69.04, 69.14; H, 8.26, 8.31.

[12,12,12-Trifluorododecyl bromide was obtained by reaction of 12-bromododecanoic acid with an excess of sulfur tetrafluoride under pressure at 125° C. for 10 hours.]

(b) 4,6-Dithia-5-[2-(12,12,12-trifluorododecyl)-phenyl]nonanedioic acid

To an ice cold solution of the aldehyde from Example 8(a) (8.65 mmoles) and 3-mercaptopropionic acid (18.93 mmoles) in methylene chloride (40 ml) was added dropwise boron trifluoride etherate (8.62 mmoles). After 15 minutes the reaction mixture was taken up in ether (150 ml) and washed with water (5×150 ml). The organic phase was dried over anhydrous magnesium sulfate and charcoal, then evaporated to leave an oil which crystallized on cooling to give the desired product as a white solid. Purification by flash chromatography over silica gel with hexane/ethyl acetate/formic acid as eluant afforded the purified product (mp 42°–44.5° C.).

Analysis for $C_{25}H_{37}F_3O_4S_2$: Calculated: C, 57.45; H, 7.13; S, 12.27. Found: C, 57,54; H, 7.07; S, 12.24.

EXAMPLE 9

Preparation of 5-(2-Dodecylphenyl)-4-sulfinyl-6-thianonanedioic acid

A solution of metachloroperbenzoic acid (2.81 mmoles) in methylene chloride (25 ml) was added dropwise over 15 minutes to an ice cold solution of 4,6-dithia-5-(2-dodecylphenyl)nonanedioic acid (2.82 mmoles), prepared as in Example 1(d), in methylene chloride (25 ml). The solution was stirred at 0° C. for 45 minutes, the volatiles were removed by evaporation and the solid residue purified by flash chromatography over silica gel using ethyl acetate/hexane/formic acid as eluant to give the desired product as an oil.

Analysis for $C_{25}H_{40}O_5S_2 \cdot \frac{1}{2}$ $H_2O$: Calculated: C, 60.82; H, 8.37; S, 12.99. Found: C, 60,89; H, 8.18; S, 12.86.

EXAMPLE 10

Preparation of 4,6-Dithia-5-[2-(8-cyclohexyloctyl)phenyl]nonanedioic acid (a) 2-(8-Cyclohexyloctyl)-benzaldehyde To an ice cold solution of 1-hexyne (49.6 mmoles) in freshly distilled tetrahydrofuran (50 ml) containing a trace of triphenylmethane was added dropwise n-butyl lithium in hexane (49.5 mmoles). About 10 minutes after the addition was stopped, sieve dried hexamethylphosphoramide (57.5 mmoles) was added and the solution stirred for 10 minutes. A solution of 2-cyclohexylethyl bromide (51.3 mmoles) in tetrahydrofuran (10 ml) was added and the reaction mixture was stirred for about 3 hours as the temperature rose to room temperature. The mixture was taken up in ether (100 ml) and washed with water (3×100 ml) and sodium chloride solution (100 ml). The organic phase was dried over magnesium sulfate and evaporated to leave an oil which was purified by flash chromatography to give 1-cyclohexyloct-3-yne. This compound (20.8 mmoles) was treated with potassium hydride (36.8 mmoles) in propylene diamine to obtain the isomeric 8-cyclohexyloct-1-yne as an oil. A mixture of 2-bromobenzaldehyde (12.59 mmoles), 8-cyclohexyloct-1-yne (14.87 mmoles), cuprous iodide (0.17 mmoles) and bis(triphenylphosphine) palladium chloride (0.26 mmoles) in triethylamine (35 ml) was refluxed under argon for 1.5 hours. The reaction mixture was cooled, filtered and the filtrate evaporated. The resulting residue was dissolved in ether (100 ml), washed with 3 N hydrochloric acid (50 ml) and saturated sodium chloride solution (50 ml) and then dried over anhydrous magnesium sulfate and charcoal. The solution was evaporated to afford an oil which was purified by flash chromatography (2% ether/hexane) to yield 2-(8-cyclohexyl-1-octynyl)benzaldehyde as an oil. This benzaldehyde (10.22 mmoles) was hydrogenated with 10% palladium on charcoal in ethyl acetate to give the desired product as an oil, after chromatography (3% ether/hexane).

Analysis for $C_{21}H_{32}O$: Calculated: C, 83.94; H, 10.73. Found: C, 82.70, 82.53; H, 10.49, 10.68.

(b) 4,6-Dithia-5-[2-(8-cyclohexyloctyl)phenyl]-nonanedioic acid

Employing the general method of Example 1(d), the compound of Example 10(a) (4.33 mmoles) was reacted with 3-mercaptopropionic acid (9.52 mmoles) in methylene chloride to yield the desired product as a white solid (mp 61°–63.5° C.), after chromatography (hexane/ethyl acetate/formic acid).

Analysis for $C_{27}H_{42}O_4S_2$: Calculated: C, 65.55; H, 8.56; S, 12.96. Found: C, 65.72; H, 8.50; S, 12.72.

EXAMPLE 11

Preparation of 4,6-Dithia-5-[2-(4-(4-butylphenyl)butyl)phenyl]-nonanedioic acid (a) 2-[4-(4-Butylphenyl)butyl]benzaldehyde Aluminum chloride (0.23 moles) was added in portions over 7 minutes to a mixture of butylbenzene (0.10 moles) and succinic anhydride (0.11 moles) in ethylene chloride (100 ml), cooled to about 13° C. Thirty minutes later the reaction mixture was poured into ice cold 3 N hydrochloric acid (250 ml) and then extracted with ethyl acetate (2×100 ml). The extract was washed with saturated sodium chloride (100 ml), dried over magnesium sulfate and evaporated to give 4-(4-butylphenyl)-4-oxobutanoic acid (mp 107°–111.5° C.). A mixture of this acid (31.63 mmoles), sulfuric acid (0.5 ml) and 10% palladium on charcoal (755 mg) in ethyl acetate (150 ml) was shaken under 50 psi hydrogen for about 15 minutes to yield the reduced product, 4-(4-butylphenyl)butanoic acid (mp 56°–58° C.). A solution of this acid (27.05 mmoles) in sieve dried tetrahydrofuran (25 ml) was reduced with ice cold diborane in tetrahydrofuran (30 mmoles) for about 1.5 hours to give 4-(4-butylphenyl)-butanol as an oil. To an ice cold solution of the butanol (27 mmoles) and carbon tetrabromide (32.56 mmoles) in methylene chloride (50 ml) was added triphenylphosphine (32.75 mmoles) in methylene chloride (50 ml) over 15 minutes. The reaction mixture was stirred for 45 minutes and then the volatiles were evaporated. The resulting oil was triturated with hexane (2×100 ml), filtered, and the filtrate evaporated and chromatographed to leave 4-(4-butylphenyl)butyl bromide as an oil.

Following the procedures of Example 1(a), (b) and (c), to 4-(4-butylphenyl)butylmagnesium bromide (from 21.47 mmoles of 4-(4-butylphenyl)butyl bromide and 18.96 mmoles of magnesium) in distilled tetrahydrofuran (35 ml) was added 2-(2-methoxyphenyl)-4,4-dimethyloxazoline (16.32 mmoles) in tetrahydrofuran (15 ml). Workup of the reaction mixture furnished 2-[2-(4-(4-butylphenyl)butyl)phenyl]-4,4-dimethyloxazoline as an oil. A solution of the oxazoline (14.41 mmoles) in methyl iodide (20 ml) was refluxed under argon for 18 hours. Removal of the volatiles afforded the corresponding 3,4,4-trimethyloxazolinium iodide as a white solid (mp 91°–94° C.). To an ice cold solution of the iodide (14.07 mmoles) in methanol was added in portions sodium borohydride (14.30 mmoles). Similar treatment of the reaction mixture resulted in the isolation of the desired benzaldehyde product as an oil.

Analysis for $C_{21}H_{26}O$: Calculated: C, 85.67; H, 8.90. Found: C, 86.06; Found, 9.19.

(b) 4,6-Dithia-5-[2-(4-(4-butylphenyl)butyl)phenyl]-nonanedioic acid

To an ice cold solution of the aldehyde from Example 11(a) (5.03 mmoles) and 3-mercaptopropionic acid (10.90 mmoles) in methylene chloride (30 ml) was added dropwise boron trifluoride etherate (5.04 mmoles). After 7 minutes the reaction mixture was taken up in ether (100 ml) and washed with water (5×100 ml). Treatment with magnesium sulfate and charcoal, followed by evaporation, left an oil which was purified by flash chromatography (silica gel and 2:1 hexane/ethyl acetate 0.5% formic acid as eluant) to give the desired product.

Analysis for $C_{27}H_{36}O_4S_2 \cdot \frac{3}{4}$ mole ethyl acetate: Calculated: C, 64.95; H, 7.63; S, 11.56. Found: C, 64.74; H, 7.31; S, 11.85.

EXAMPLE 12

Preparation of 4,6-Dithia-5-[2-(1-trans-dodecenyl)phenyl]nonanedioic acid (a) 2-(1-trans-dodecenyl)benzaldehyde To a suspension of lithium aluminum hydride (22.2 mmoles) in tetrahydrofuran (30 ml) under argon, cooled to 0° C., was added 2-(1-dodecyn-1-yl) benzaldehyde (11.1 mmoles, prepared as in Example 4(a) in tetrahydrofuran (10 ml), dropwise with stirring. After coming to room temperature, the reaction mixture was refluxed for 18 hours. The reaction mixture was then cooled to 0° C., ice was added, followed by ether and dilute hydrochloric acid, and the layers were separated. The organic layer was washed with water and brine. The dried solution was concentrated to give 2-(1-trans-dodecenyl)benzyl alcohol, after recrystallization from acetonitrile. The benzyl alcohol (0.080 mmoles) was dissolved in ethyl acetate (10 ml) under argon and manganese dioxide (12.6 mmoles) was added. The reaction mixture was stirred for 18 hours at room temperature, filtered and the filtrate concentrated to leave an oil which is the desired product.

(b) 4,6-Dithia-5-[2-(1-trans-1-dodecenyl)phenyl]-nonanedioic acid

Employing the general method of Example 1(d), the compound of Example 12(a) (0.771 mmoles) was reacted with mercaptopropionic acid (1.7 mmoles) to yield the desired product as a white solid, mp 37°–40° C.

Analysis for $C_{25}H_{38}O_4S_2$: Calculated: C, 64.34; H, 8.21. Found: C, 64.52; H, 8.20.

EXAMPLE 13

Preparation of 4,6-Dithia-5-[2-(11-dodecynyl)phenyl]nonanedioic acid (a) 2-(11-Dodecynyl)benzaldehyde To a solution of trimethylsilylacetylene (66.6 mmoles) in tetrahydrofuran (25 ml) cooled to −15° C., under argon, was added dropwise n-butyl lithium (25.6 ml of 2.6 moles in hexane). The resulting solution was stirred for 15 minutes and hexamethylphosphoramide (25 ml) was added. After stirring for 15 minutes the solution was cooled further to −78° C. and decyl dibromide (66.6 mmoles) in tetrahydrofuran (150 ml) was added all at once. The reaction mixture was allowed to warm to room temperature and then poured into ice water/ether. The organic layer was washed with water and saturated sodium chloride solution, dried and concentrated. The residual product was purified by flash chromatography (silica column, eluted with hexane) to give trimethylsilyl 11-dodecynyl bromide. This compound (26.15 mmoles) in tetrahydrofuran (50 ml) was added to magnesium turnings (22.35 mmoles) and to the resulting Grignard reagent was added 2-(2-methoxyphenyl)4,4-dimethyloxazoline (14.9 mmoles) in tetrahydroduran (30 ml). The solution was stirred under argon at room temperature for 18 hours, cooled and aqueous ammonium chloride was added dropwise. The reaction mixture was diluted with water and ether, and the organic layer was dried and evaporated to leave the product which was purified by flash chromatography to give 2-(trimethylsilyl 11-dodecynylphenyl)-4,4-dimethyloxazoline. A solution of this compound (7.36 mmoles) in methyl iodide (25 ml) was refluxed for 15 hours. The volatiles were removed under vacuum to leave the semi-solid 2-(trimethylsilyl 11-dodecynylphenyl)-3,4,4-trimethyloxazolinium iodide. To a cooled solution (0° C.) of this compound (6.96 mmoles) in methanol (30 ml) was added in portions sodium borohydride (7.30 mmoles). The reaction mixture was stirred for 30 minutes and was then quenched with 5% sodium hydroxide solution. The product was extracted into ether and the dried extract was concentrated to leave an oil which was dissolved in acetone (50 ml). Hydrochloric acid (10 ml, 3 N) was added and the mixture was stirred at room temperature for 18 hours. The acetone was removed in vacuo and the residue partitioned between water and ether. The organic layer was dried and concentrated to give the product which was purified by flash chromatography to give as an oil, 2-(trimethylsilyl 11-dodecynyl)benzaldehyde. This compound (2.86 mmoles) was dissolved in methanol (10 ml) under argon, and potassium carbonate (100 mg) was added. The mixture was stirred at room temperature for 18 hours and the solvent removed in vacuo. The residue was dissolved in methylene chloride and the solution washed with 5% sodium bicarbonate solution, water and brine. The dried solution was concentrated to give the desired 2-(11-dodecynyl)benzaldehyde as an oil.

(b) 4,6-Dithia-5-[2-(11-dodecynyl)phenyl]nonanedioic acid

Employing the general method of Example 1(d), the compound of Example 13(a) (2.73 mmoles) was reacted with mercaptopropionic acid (6.01 mmoles) to yield the product as a white solid, mp 34°-38° C.

Analysis for $C_{25}H_{36}O_4S_2$: Calculated: C, 64.62; H, 7.81. Found: C, 64.51; H, 7.80.

EXAMPLE 14

Preparation of 4,6-Dithia-5-[2-(8-phenyloctyl)-5-trifluoromethyl-phenyl]nonanedioic acid (a) 2-(8-Phenyloctyl)-5-trifluoromethyl benzaldehyde To a solution of 2-bromo-5-trifluoromethyl benzonitrile (20.16 mmoles) in methylene chloride (50 ml), under argon at room temperature, was added diisobutylaluminum hydride (25 mmoles, 25 ml hexane) dropwise and the resulting solution was stirred for 30 minutes. The reaction mixture was diluted with ether (50 ml), cooled in ice and quenched by the careful addition of hydrochloric acid (50 ml, 3 N). The ice bath was removed and the mixture was stirred vigorously for 15 minutes. The organic layer was washed with brine (50 ml), treated with magnesium sulfate-charcoal and evaporated. The resulting oil was purified by distillation to give 2-bromo-5-trifluoromethyl benzaldehyde, bp 50°-55° C. at 0.05 mm Hg. A mixture of this compound (16.24 mmoles), 1-phenylocta-1,7-diyne (19.54 mmoles, prepared as in Example 7b), cuprous iodide (0.19 mmoles) and bis(triphenylphosphine) palladium chloride (0.34 mmoles) in triethylamine (50 ml) was refluxed under argon for 30 minutes. The reaction mixture was cooled and filtered. The filtrate was evaporated, taken up in ether (100 ml), washed with hydrochloric acid (50 ml, 3 N) and sodium chloride, and treated with magnesium sulfate-charcoal. Filtration and evaporation left an oil which was purified by flash chromatography (5% ether/hexane) to yield 2-(8-phenyloctadiyn-1,7-yl)-5-trifluoromethyl benzaldehyde as an oil. A solution of this compound (13.26 mmoles) in ethyl acetate (100 ml) was treated with charcoal for 30 minutes and then filtered. The solution was then shaken under 50 psi of hydrogen with 10% palladium on charcoal (502 mg) for about 90 minutes. Thin layer chromatography of the reaction mixture indicated about 50% reduction of the aldehyde to the alcohol. To re-oxidize the alcohol, the palladium catalyst was filtered off and manganese dioxide (20 g) was added. This mixture was then stirred at room temperature under argon for 18 hours. Filtration and evaporation gave an oil which was purified by flash chromatography (2% ether/hexane) to afford 2-(8-phenyloctyl)-5-trifluoromethyl benzaldehyde as an oil.

(b) 4,6-Dithia-5-[2-(8-phenyloctyl)-5-trifluoromethyl-phenyl]nonanedioic acid

Employing the general method of Example 1(d), the compound of Example 14(a) (2.75 mmoles) was reacted with mercaptopropionic acid (5.97 mmoles) to yield the desired product as a pale yellow liquid. It was converted to the dipotassium salt by dissolving in potassium carbonate solution (15 ml, 0.3 M) and isolated by lyophilization.

Analysis for $C_{28}H_{33}F_3O_4S_2K_2$: Calculated: C, 53.14; H, 5.26. Found: C, 52.97; H, 5.29.

Similarly, following the procedures of Example 14(a) and (b), 3-bromobenzaldehyde (5.13 mmoles) was reacted with 1-phenylocta-1,7-diyne (6.04 mmoles) to yield 3-(8-phenyloctadiyn-1,7-yl)benzaldehyde which was reduced/oxidized to 3-(8-phenyloctyl)benzaldehyde and the latter (1.87 mmoles) was reacted with mercaptopropionic acid (4.02 mmoles) to give 4,6-dithia-5-[3-(8-phenyloctyl)phenyl]nonanedioic acid, mp 56°-60° C.

EXAMPLE 15

Preparation of 4,6-Dithia-5-[2-(5-(4-acetyl-3-hydroxy-2-propylphenoxy)-pentoxy)-phenyl]nonanedioic acid (a) 2-[5-(4-acetyl-3-hydroxy-2-propylphenoxy)pentoxy]benzaldehyde A solution of salicylaldehyde (82 mmoles) in acetone (50 ml) was added dropwise to a refluxing solution of 1,5-dibromopentane (90.2 mmoles), potassium carbonate (90.2 mmoles) and potassium iodide (0.4 g) in acetone (200 ml). The mixture was refluxed for 18 hours, filtered and the filtrate concentrated. The residue was dissolved in ether and washed with cold 10% sodium hydroxide solution, water and brine. The organic layer was dried over magnesiun sulfate and concentrated. The product was purified by flash chromatography (4% ethyl acetate/hexane) to give 2-(5-bromopentoxy)benzaldehyde. A mixture of this compound (11.1 mmoles), 4-acetyl-3-hydroxy-2-propyl phenol (11.62 mmoles) and potassium carbonate (5.55 mmoles) in acetone (30 ml) was refluxed for 5 days, stirred at room temperature for 2 days and then refluxed for 24 hours. The suspension was cooled to room temperature, filtered and the filtrate concentrated. The residue was dissolved in ethyl acetate and then washed with ice-cold 5% sodium hydroxide solution, water and brine. The dried solution was concentrated and the product flash chromatographed to give the desired product.

(b) 4,6-Dithia-5-[2-(5-(4-acetyl-3-hydroxy-2-propylphenoxy)-pentoxy)phenyl]nonanedioic acid Employing the general procedure of Example 1(d), the compound of Example 15(a) (2.6 mmoles) was reacted with mercaptopropionic acid (5.2 mmoles) to yield the desired product as a yellow liquid. It was converted to the disodium salt by dissolving in sodium carbonate solution (0.5 M) and isolated by lyophilization, mp 146°-148° C. (dec).

Analysis for $C_{29}H_{36}O_8S_2Na_2 \cdot \frac{3}{4}H_2O$: Calculated: C, 54.75; H, 5.94; S, 10.08. Found: C, 54.51; H, 5.80; S, 10.12.

EXAMPLE 16

Preparation of 4,6-Dithia-5-[2-(7-phenylthioheptyl)phenyl]nonanedioic acid (a) 2-(7-Bromoheptyl)benzoic acid Diisopropylamine (61.8 ml, 441 mmoles) was dissolved in tetrahydrofuran (200 ml) and cooled to 0° C. in an ice-methanol bath while stirring under argon. A 2.6 M solution of n-butyllithium in hexane (170 ml, 441 mmoles) was added dropwise. Toluic acid (30.0 g, 221 mmoles) was then added and the reaction immediately turned a deep red color. This mixture was added slowly to a solution of 1,6-dibromohexane (84 ml, 551 mmoles) in tetrahydrofuran (200 ml) at 0° C. Following the addition, the ice bath was removed and the reaction mixture was stirred at room temperature under argon for 18 hours. The solvent was evaporated and the residue dissolved in ether. The ether was extracted with cold 1 N sodium hydroxide solution. The pH of the aqueous phase was adjusted to 8.0 with cold concentrated hydrochloric acid and extracted with ether. The ether extract was dried over anhydrous magnesium sulfate, filtered and evaporated to afford the desired product.

(b) 2-(7-Phenylthioheptyl)benzoic acid

The compound of Example 16(a) (2.5 g, 8 mmoles) was dissolved in dimethylformamide (50 ml), to which was added a mixture of thiophenol (1.3 ml, 12.6 mmoles) and triethylamine (4.7 ml, 33 mmoles) in dimethylformamide (50 ml). The reaction mixture was heated to 80° C. for 1-2 hours. The solvents were evaporated and the residue flash chromatographed on silica gel eluted with 15% ethyl acetate in hexane plus 1% formic acid to provide the desired product.

(c) 2-(7-Phenylthioheptyl)benzyl alcohol

To a suspension of lithium aluminum hydride (0.292 g, 7 mmoles) in tetrahydrofuran (30 ml) was added a solution of the compound of Example 16(b) (2.39 g, 7 mmoles) in tetrahydrofuran (30 ml). The reaction mixture was stirred at room temperature under argon for 18 hours. Several drops of ice water were added, followed by cold 10% sodium hydroxide solution (1.0 ml) followed by more ice water. The precipitate was filtered and washed, and the filtrate was dried over magnesium sulfate, filtered and evaporated. The crude alcohol was flash chromatographed on silica gel with 10% ethyl acetate in hexane to give the desired product.

(d) 2-(7-Phenylthioheptyl)benzaldehyde

To a suspension of manganese dioxide (11.78 g, 135 mmoles) in ethyl acetate (30 ml) was added a solution of the compound of Example 16(c) (11.78 g, 3.7 mmoles) in ethyl acetate (20 ml). The reaction mixture was stirred at room temperature under argon for 1.5 hours. The suspension was filtered, and the filtrate was dried over magnesium sulfate, filtered and evaporated to give the product.

(e) 4,6-Dithia-5-[2-(7-phenylthioheptyl)phenyl]nonanedioic acid.

The compound of Example 16(d) was dissolved in methylene chloride (5.0 ml), cooled to 0° C. and mercaptopropionic acid (0.123 ml, 1.3 mmoles) was added, followed by boron trifluoride etherate (0.182 g, 1.3 mmoles). The reaction mixture was stirred under argon for 5-10 minutes. The solvents were evaporated and the residue was dissolved in carbon tetrachloride and washed with water. The organic phase was dried over magnesium sulfate, filtered and evaporated to give the desired product.

Analysis for $C_{26}H_{34}O_4S_3$: Calculated: C, 61.63; H, 6.76;. S. 18.98. Found: C, 61.59; H, 6.87; S, 18.90.

Similarly, following the procedures of Example 16(b)–(e), the indicated substituted thiophenols are employed to give the corresponding products:

| Substituted thiophenol | Product |
|---|---|
| 4-fluorothiophenol | 4,6-dithia-5-[2-(7-(4-fluorophenylthio)heptyl)phenyl]-nonanedioic acid |
| 4-bromothiophenol | 4,6-dithia-5-[2-(7-(4-bromophenylthio)heptyl)phenyl]-nonanedioic acid |
| 4-methoxythiophenol | 4,6-dithia-5-[2-(7-(4-methoxyphenylthio)heptyl)phenyl]-nonanedioic acid |
| 3-trifluoromethylthiophenol | 4,6-dithia-5-[2-(7-(3-trifluoromethylphenylthio)-heptyl)phenyl]nonanedioic acid |
| 4-trifluoromethylthiophenol | 4,6-dithia-5-[2-(7-(4-trifluoromethylphenylthio)heptyl)-phenyl]nonanedioic acid |

EXAMPLE 17

Preparation of 4,6-Dithia-5-[2-(8-phenyl-7(Z)-octenyl)phenyl]-nonanedioic acid (a) 7-(2-Carboxyphenyl)heptyl-1-triphenylphosphonium bromide To a mixture of the compound of Example 16(a) (10.0 g, 34 mmoles) in toluene (50 ml) was added a solution of triphenylphosphine (9.68 g, 37 mmoles) in toluene (50 ml). The reaction mixture was heated to 80° C. and stirred under argon for 3 days. The separated oil was removed and the solvent evaporated to give the phosphonium bromide.

(b) 2-(8-Phenyl-7(Z)-octenyl)benzoic acid

A mixture of the compound of Example 17(a) (1.4 g, 4.5 mmoles) and tetrahydrofuran (15 ml) under argon was cooled to −78° C. with a dry ice acetone bath. A 2.6 M solution of n-butyllithium in hexane (3.55 ml, 9 mmoles) was added dropwise. The resulting red-orange solution was stirred at −78° C. for 30 minutes. Hexamethylphosphoramide (5.5 ml) was added in one portion followed by benzaldehyde (0.41 ml, 4 mmoles) in tetrahydrofuran (5 ml). The reaction mixture was stirred under argon for 30 minutes. The tetrahydrofuran was evaporated and the residue was dissolved in ether and washed with cold 3 N hydrochloric acid. The combined organic phase was dried over magnesium sulfate, filtered and evaporated. The crude material was then chromatographed on silica gel eluted with 4% ethyl acetate in hexane plus 1% formic acid to yield the desired compound.

(c) 4,6-Dithia-5-[2-(8-phenyl-7(Z)-octenyl) phenyl]-nonanedioic acid

Employing the procedures of Example 16(c)–(e), the compound of Example 17(b) was reduced with lithium aluminum hydride, the benzyl alcohol was oxidized with manganese dioxide and the benzaldehyde was reacted with mercaptopropionic acid to yield the desired product, whose identity was verified by nuclear magnetic resonance, thin layer chromatography and mass spectra data.

EXAMPLE 18

Preparation of 4,6-Dithia-5-[2-(8-(4-trifluoromethylphenyl)octyl)-phenyl]nonanedioic acid (a) 2-[8-(4-trifluoromethylphenyl)-7(Z)-octenyl]benzyl alcohol Employing the procedure of Example 17(b), the compound of Example 17(a) is treated with n-butyllithium followed by 4-trifluoromethylbenzaldehyde to give 2-[8-(4-trifluoromethylphenyl)-7(Z)-octenyl]benzoic acid which is reduced with lithium aluminum hydride to give the desired benzyl alcohol.

(b) 2-[8-(4-Trifluoromethylphenyl)octyl]benzaldehyde

A mixture of methanol (200 ml), 10% palladium on charcoal (3.0 mg) and the compound of Example 18(a) (288.9 mg, 0.8 mmole) was hydrogenated in a Parr bottle until the reaction was complete as determined by nuclear magnetic resonance. The reaction mixture was filtered, washed and the filtrate concentrated to yield 2-[8-(4-trifluoromethylphenyl)octyl]benzyl alcohol. The latter was oxidized, employing the procedure of Example 16(d), with manganese dioxide to give the desired product.

(c) 4,6-Dithia-5-[2-(8-(4-trifluoromethylphenyl)octyl)phenyl]nonanedioic acid

Employing the procedure of Example 16(e), the compound of Example 18(b) was reacted with mercaptopropionic acid to yield the desired product.

Analysis for $C_{28}H_{35}F_3O_4S_2.\frac{1}{2}H_2O$: Calculated: C, 59.45; H, 6.41. Found C, 59.33; H, 6.29.

Similarly, following the procedures of Example 18(a)-(c), the indicated substituted benzaldehydes are employed to give the corresponding products:

| Substituted benzaldehyde | Product |
|---|---|
| 4-fluorobenzaldehyde | 4,6-dithia-5-[2-(8-(4-fluorophenyl)octyl)phenyl] nonanedioic acid |
| 4-bromobenzaldehyde | 4,6-dithia-5-[2-(8-(4-bromophenyl)octyl)phenyl]-nonanedioic acid |
| 4-methoxybenzaldehyde | 4,6-dithia-5-[2-(8-(4-methoxyphenyl)octyl)-phenyl]nonanedioic acid |
| 3-trifluoromethylbenzaldehyde | 4,6-dithia-5-[2-(8-(3-trifluoromethylphenyl)octyl)-phenyl]nonanedioic acid |

EXAMPLE 19

As a specific embodiment of a composition of this invention, an active ingredient, such as the compound of Example 1(d), is dissolved in 25 mM sodium carbonate at a concentration of 0.4 percent and aerosolized from a nebulizer operating at an air flow adjusted to deliver the desired aerosolized weight of drug.

EXAMPLE 20

As an additional specific embodiment of a composition of this invention, an active ingredient, such as the compound of Example 2(b), is admixed with mannitol at a concentration of 1.0 percent and administered from a powder inhalation device adjusted to deliver the desired weight of drug.

What is claimed is:

1. A compound represented by the following structural formula (I):

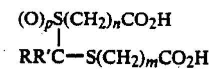

(I)

wherein m is 1 or 2; n is 1, 2 or 3; R' is hydrogen or methyl; R is a radical selected from the group consisting of:

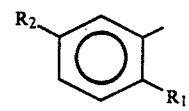

or wherein $R_1$ is $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecynyl, 1-trans-dodecenyl, 5-(4-acetyl-3-hydroxy-2-propylphenoxy)pentoxy, 2(Z), 5(Z)-undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl-CH=CH-$(CH_2)_{2-8}$, phenyl-$C_3$ to $C_9$ alkoxy, trifluoromethyl-$C_7$ to $C_{12}$ alkyl, cyclohexyl-$C_4$ to $C_{10}$ alkyl or wherein each q is 0, 1, 2 or 3 but the sum of both q's does not exceed 3, and $R_2$ is hydrogen, bromo, chloro, methyl, trifluoromethyl, methoxy or nitro; or $R_1$ is hydrogen and $R_2$ is $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecynyl, 1-trans-dodecenyl, 5-(4-acetyl-3-hydroxy-2-propylphenoxy)pentoxy, 2(Z),5(Z)-undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl —CH=CH—$(CH_2)_{2-8}$, phenyl-$C_3$ to $C_9$ alkoxy, trifluoromethyl-$C_7$ to $C_{12}$ alkyl, cyclohexyl-$C_4$ to $C_{10}$ alkyl, or wherein each q is 0, 1, 2 or 3 but the sum of both q's does not exceed 3, and p is 0 or 1, with the proviso that R is not a thiophene radical and any of $R_1$ and $R_2$ above are not thioalkyl or phenylthioalkyl when p is 1; or a pharmaceutically acceptable salt thereof.

2. A compound of claim 1 represented by the following structural formula (II):

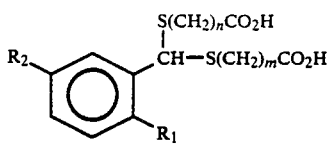

or a pharmaceutically acceptable salt thereof.

3. A compound of claim 2 represented by the following structural formula (III):

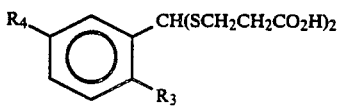

wherein $R_3$ is selected from the group consisting of $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecynyl, 1-trans-dodecenyl, 5-(4-acetyl-3-hydroxy-2-propylphenoxy)pentyl, 2(Z),5(Z)-undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl—CH=CH—$(CH_2)_{2-8}$, phenyl-$C_3$ to $C_9$ alkoxy, trifluoromethyl-$C_7$ to $C_{12}$ alkyl, cyclohexyl-$C_4$ to $C_9$ alkyl and

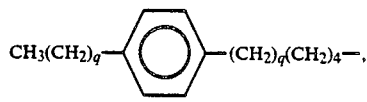

wherein each q is 0, 1, 2 or 3 but the sum of both q's does not exceed 3, and $R_4$ is hydrogen, bromo, chloro, methyl, trifluoromethyl, methoxy or nitro.

4. A compound of claim 3 wherein $R_4$ is hydrogen.

5. A compound of claim 4 wherein $R_3$ is an alkyl radical containing 8 to 13 carbon atoms.

6. A compound of claim 5 which is 4,6-dithia-5-(2-dodecylphenyl)nonanedioic acid; 4,6-dithia-5-(2-decylphenyl)nonanedioic acid; or 4,6-dithia-5-(2-octylphenyl)nonanedioic acid.

7. A compound of claim 4 wherein $R_3$ is an alkoxy radical containing 7 to 12 carbon atoms.

8. A compound of claim 7 which is 4,6-dithia-5-(2-nonyloxyphenyl)nonanedioic acid or 4,6-dithia-5-(2-undecyloxyphenyl)nonanedioic acid.

9. A compound of claim 4 which is 4,6-dithia-5-(2-undecylthiophenyl)nonanedioic acid; 4,6-dithia-5-[2-(1-dodecyn-1-yl)phenyl]nonanedioic acid; 4,6-dithia-5-[2-(2(Z),5(Z)-undecadienyloxy)phenyl]nonanedioic acid; 4,6-dithia-5-[2-(8-cyclohexyloctyl)phenyl]nonanedioic acid; or 4,6-dithia-5-[2-(4-butylphenyl)butyl]phenyl]nonanedioic acid.

10. A compound of claim 4 wherein $R_3$ is a phenyl-$C_4$ to $C_{10}$ alkyl radical with the phenyl optionally mono substituted with bromo, chloro, trifluoromethyl, methoxy, methylthio or trifluoromethylthio, phenylthio-$C_3$ to $C_9$ alkyl radical with the phenyl optionally mono substituted with bromo, chloro, trifluoromethyl, methoxy, methylthio or trifluoromethylthio, phenyl-CH=CH—$(CH_2)_{2-8}$ radical or phenyl-$C_3$ to $C_9$ alkoxy radical.

11. A compound of claim 10 which is 4,6-dithia-5-[2-(8-phenyloctyl)phenyl]nonanedioic acid; 4,6-dithia-5-[2-(6-phenylhexyloxy)phenyl]nonanedioic acid; 4,6-dithia-5-[2-(8-(4-trifluoromethylphenyl)octyl)phenyl]nonanedioic acid; 4,6-dithia-5-[2-(7-phenylthioheptyl)phenyl]nonanedioic acid; or 4,6-dithia-5-[2-(8-phenyl-7(Z)-octenyl)phenyl]nonanedioic acid.

12. A compound of claim 4 which is 4,6-dithia-5-[2-(12,12,12-trifluorododecyl)phenyl]nonanedioic acid; 4,6-dithia-5-[2-(11-dodecynyl)phenyl]nonanedioic acid; 4,6-dithia-5-[2-(1-trans-dodecenyl)phenyl]nonanedioic acid; or 4,6-dithia-5-[2-(5-(4-acetyl-3-hydroxy-2-propylphenoxy)pentoxy)phenyl]nonanedioic acid.

13. A compound of claim 3 wherein $R_4$ is bromo, chloro, methyl, trifluoromethyl, hydroxy, methoxy or nitro.

14. A compound of claim 13 which is 4,6-dithia-5-(5-methoxy-2-undecyloxyphenyl)nonanedioic acid; 4,6-dithia-5-(5-bromo-2-undecyloxyphenyl)nonanedioic acid; 4,6-dithia-5-(5-nitro-2-undecyloxyphenyl)nonanedioic acid; or 4,6-dithia-5-(5-hydroxy-2-undecyloxyphenyl)nonanedioic acid.

15. A compound of claim 13 which is 4,6-dithia-5-[2-(8-phenyloctyl)-5-trifluoromethylphenyl]nonanedioic acid.

16. A compound of claim 2 represented by the following structural formula (IV):

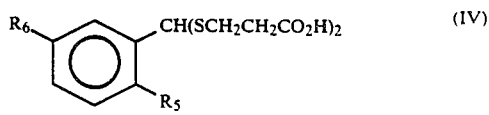

wherein $R_5$ is hydrogen and $R_6$ is selected from the group consisting of $C_8$ to $C_{13}$ alkyl, $C_7$ to $C_{12}$ alkoxy, $C_7$ to $C_{12}$ thioalkyl, $C_{10}$ to $C_{12}$ 1-alkynyl, 11-dodecynyl, 1-trans-dodecenyl, 5-(4-acetyl-3-hydroxy-2-propylphenoxy)pentoxy, 2(Z),5(Z)-undecadienyloxy, phenyl-$C_4$ to $C_{10}$ alkyl with the phenyl optionally mono substituted with bromo, chloro, trifluoromethyl, methoxy, methylthio or trifluoromethylthio, phenylthio-$C_3$ to $C_9$ alkyl with the phenyl optionally mono substituted with bromo, chloro, trifluoromethyl, methoxy, methylthio or trifluoromethylthio, phenyl-CH=CH—$(CH_2)_{2-8}$, phenyl-$C_3$ to $C_9$ alkoxy, trifluoromethyl-$C_7$ to $C_{12}$ alkyl, cyclohexyl-$C_4$ to $C_{10}$ alkyl and

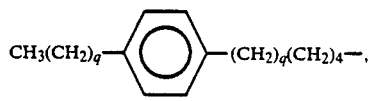

wherein each q is 0, 1, 2 or 3 but the sum of both q's does not exceed 3.

17. A compound of claim 16 which is 4,6-dithia-5-(3-undecyloxyphenyl)nonanedioic acid; 4,6-dithia-5-(3-nonyloxyphenyl)nonanedioic acid; 4,6-dithia-5-[3-(2(Z),5(Z)-undecadienyloxy)phenyl]nonanedioic acid or 4,6-dithia-5-[3-(8-phenyloctyl)phenyl]nonanedioic acid.

18. A compound of claim 1 represented by the following structural formula (V):

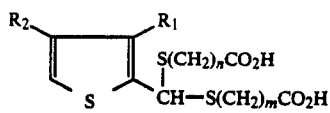 (V)

or a pharmaceutically acceptable salt thereof.

19. A compound of claim 18 which is 4,6-dithia-5-(3-dodecyl-2-thienyl)nonanedioic acid; or 4,6-dithia-5-(4-dodecyl-2-thienyl)nonanedioic acid.

20. A compound of claim 1 which is 4,6-dithia-5-methyl-5-(2-undecyloxyphenyl)nonanedioic acid; or 5-(2-dodecylphenyl)-4-sulfinyl-6-thianonanedioic acid.

21. A pharmaceutical composition for inhibiting the effects of leukotriene comprising a pharmaceutical carrier or diluent and a nontoxic amount sufficient to produce said inhibition of a compound of claim 1, formula (I).

22. A pharmaceutical composition according to claim 21 in the form of an aerosol formulation or a sterile solution, or in a form suitable for administration by inhalation, parenteral administration or topical administration.

* * * * *